United States Patent [19]
Lavigne

[11] 4,065,424
[45] Dec. 27, 1977

[54] LACTONES AND ESTER DERIVATIVES THEREOF

[75] Inventor: Joe B. Lavigne, Oakland, Calif.

[73] Assignee: Chevron Research Company, San Francisco, Calif.

[21] Appl. No.: 758,389

[22] Filed: Jan. 11, 1977

Related U.S. Application Data

[62] Division of Ser. No. 549,612, Feb. 13, 1975.

[51] Int. Cl.$^2$ .................................................. C08K 5/12
[52] U.S. Cl. ........................ 260/31.8 DB; 260/514 K; 560/122
[58] Field of Search ...... 260/468 K, 514 K, 31.8 DB, 260/31.8 C

*Primary Examiner*—Paul R. Michl
*Attorney, Agent, or Firm*—D. A. Newell; John Stoner, Jr.

[57] ABSTRACT

Spirodilactones from alkenyl or alkyl bis(succinic anhydride) and acids and alkyl esters thereof.

1 Claim, No Drawings

LACTONES AND ESTER DERIVATIVES THEREOF

This is a division of application Ser. No. 549,612, filed Feb. 13, 1975.

BACKGROUND OF THE INVENTION

1. Field of the Invention

The present invention relates to lactones, acids and esters. More particularly, the invention relates to spirodilactones from alkenyl or alkyl bis(succinic anhydride) and acids and alkyl esters thereof.

2. Description of the Prior Art

Lactones are intra-molecular esters usually formed from hydroxy and halogenated carboxylic acids in which the hydroxyl (or halogen) and carboxyl groups are located in positions to lose water or halogen acid. See, for instance, Kirk-Othmer "Encyclopedia of Chemical Technology," section entitled "Lactones."

Higher dilactones are prepared by the oxidation of higher carbocyclic ketones, as well as other methods. Such higher dilactones are useful in the production of perfumes. See, for instance, U.S. Pat. No. 2,301,827.

Poly(ester lactones) have been prepared from alkenyl succinic anhydrides and polyhydric alcohols. Such ester lactones are useful as plasticizers. See, for instance, U.S. Pat. No. 3,155,686.

SUMMARY OF THE INVENTION

In accordance with the present invention there are provided higher spirodilactones and acids and alkyl esters thereof having the structural formulas

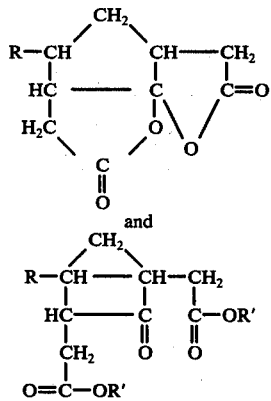

in which R is alkyl or alkenyl of 2 to 28 carbon atoms and R' groups, which may be the same or different, are hydrogen or alkyl groups of 1 to 20 carbon atoms each.

The novel spirodilactones and cyclic keto acids and esters thereof of the invention are multifunctional: the acids are useful as petroleum composition rust inhibitors, the esters as plasticizers and the lactones as intermediates in the preparation of paper sizes, resins, polymers, etc.

DESCRIPTION OF THE PREFERRED EMBODIMENTS

Alkenyl bis(succinic anhydride) compounds, hereinafter noted as ABSA for convenient reference, are prepared by reacting one mol of monoolefinic aliphatic hydrocarbon of from about 3 to 30 carbon atoms with 2 moles of 2,3-unsaturated-1,4-dicarboxylic acid anhydrides. The reaction of the monoolefinic hydrocarbon with the unsaturated dicarboxylic acid anhydride is thermal and noncatalytic. The reactants are heated at a temperature of at least about 150° C, but below the decomposition temperatures at which $CO_2$ is formed.

The spirodilactone from alkyl or alkenyl bis(succinic anhydride) of the present invention is prepared by heating alkyl or alkenyl bis(succinic anhydride) to effect removal of $CO_2$. One mol of $CO_2$ is lost, and the novel spirodilactone results in accordance with the following schematic equation and structural formulas, using the alkenyl analog for illustration:

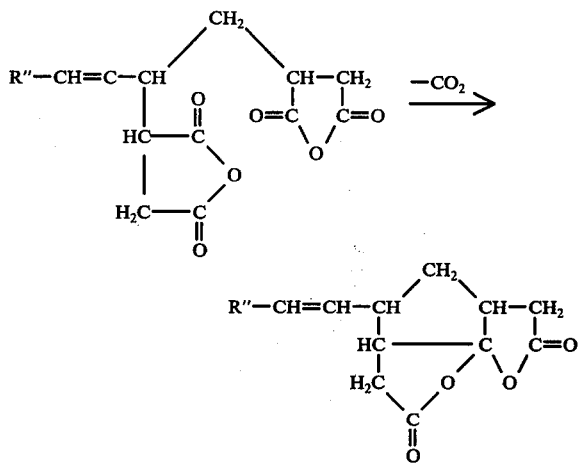

in which R" is hydrogen or alkyl of 1 to 26 carbon atoms.

In the case of propenyl or isobutenyl bis(succinic anhydride), the dilactone has the schematic formula:

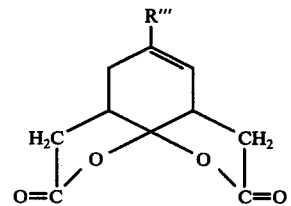

in which R''' is hydrogen or a methyl group.

The cyclic keto esters have the schematic formula:

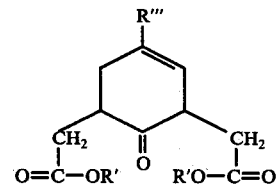

in which R''' is hydrogen or a methyl group and R' groups, which may be the same or different, are hydrogen or alkyl groups of 1 to 20 carbon atoms each.

The cyclic keto diester of the spirodilactone of the present invention is prepared by conventional transesterification with alcohol. The alcohols may be aliphatic or cycloaliphatic alcohols of 1 to 20 carbon atoms. However, preferred alcohols are the alkyl alcohols of from 1 to 8 carbon atoms, since the esters derived therefrom are particularly suited as plasticizers.

The following examples further illustrate the preparation of the novel spirodilactones from alkenyl bis(succinic anhydride) and acids and esters thereof in accordance with the present invention. Unless otherwise indicated, percentages are on a weight basis.

EXAMPLES

EXAMPLE 1

PREPARATION OF $C_8$ ABSA

Octenyl succinic anhydride (1383 g, 6.6 mols) and maleic anhydride (429 g, 4.4 mols) were placed in a 2-liter round-bottom flask equipped with stirrer, condenser and thermometer. The reaction was carried out for 18 hours by heating with stirring in an oil bath at 200° C. The product was distilled through a wiped-film evaporator at 140° C and 0.5–1 mm Hg to remove unconverted octenyl succinic anhydride and maleic anhydride. The $C_8$ ABSA was left as a bottoms product (1000 g, 3.2 mols). The ABSA is characterized by carbonyl absorption peaks in the infrared at 1770 cm$^{-1}$ and 1855 cm$^{-1}$.

EXAMPLE 2

Thermal Preparation of Spirodilactone from $C_8$ ABSA

The $C_8$ ABSA (100 g) was charged to a vacuum distillation apparatus equipped with a 2-tray Oldershaw column and reflux condenser. Heating was by means of an oil bath. The reaction flask was immersed in the hot oil at a temperature of 250°–270° C for a period of about 2.5 hours, during which gas evolved and the following fractions of liquid overhead were collected:

| Fraction | Flask °C | Overhead, °C | Vacuum, mm Hg | Weight, g |
|---|---|---|---|---|
| 1 | 256–245 | 150–227 | 6–2.5 | 10.6 |
| 2 | 245–250 | 214–222 | 2.2 | 21.6 |
| 3 | 250–260 | 217–211 | 2.1 | 9.1 |

The overhead product from the above reaction and one other run from the same feed were combined (48.6 g total) and distilled through a short-path microstill. The following fractions were collected:

| Fraction | Bath, °C | Overhead, °C | Vacuum, mm Hg | Weight, g |
|---|---|---|---|---|
| 1 | 205–210 | 118–198 | 0.4–0.8 | 8.7 |
| 2 | 214 | 203–206 | 0.8 | 19.3 |
| 3 | 215–233 | 223–228 | 2.1–2.2 | 11.8 |
| 4 | 239–255 | 230 | 2.1–2.2 | 6.1 |
| Bottoms | — | — | — | 1.9 |

The molecular weight of the overhead product was measured by high-resolution mass spectrometry as 264.1365. The theoretical molecular weight for the spirodilactone from $C_8$ ABSA is 264.1362, corresponding to the formula $C_{15}H_{20}O_4$. The spirodilactone has a carbonyl absorption in the infrared spectrum of 1790 cm$^{-1}$. The presence of a trans-double bond was shown by a 1666 cm$^{-1}$ absorption in the Raman spectrum of fraction number 2.

EXAMPLE 3

Spirodilactone from $C_3$ ABSA

Propenyl bis(succinic anhydride) (100 g) contained in a 100-ml round-bottom flask equipped with a microstill head was heated in a oil bath, and the following fractions were collected:

| Fraction | Flask °C | Vacuum, mm Hg | Weight, g |
|---|---|---|---|
| 1 | 225–232 | 5.5 | 3.5 |
| 2 | 225–232 | 5.5–2 | 4.0 |
| 3 | 227–235 | 2–1 | 4.4 |
| 4 | 235–250 | 1.5–2 | 4.8 |

Infrared spectra indicated that Fractions 2–4 were essentially identical and were a mixture of spirodilactone, anhydride and a product containing free carboxylic acid groups.

In accordance with the present invention, it has also been found that the formation of the spirodilactones is substantially accelerated by having a base present. In general, organic bases, e.g., heterocyclic or trialkyl tertiary amines, or quaternary ammonium hydroxides are preferred, but other bases such as potassium cyanide and sodium hydroxide may be used. Typical experiments showing the catalytic effect of bases are given in the following examples.

EXAMPLE 4

Catalytic Formation of the Spirodilactone from $C_8$ ABSA

The effect of additives on the formation of spirodilactone was evaluated by placing 1 g of $C_8$ ABSA in a Fischer-Porter pressure tube of volume 94 ml and equipped with a pressure gauge, inlet valve and outlet valve. The tube was heated by immersion in an oil bath. After the ABSA and catalyst were placed in the tube, it was flushed with nitrogen several times, degassed under vacuum, and placed under nitrogen at atmospheric pressure. It was then placed in an oil bath at the desired temperature and the reaction time, bath temperature, and pressure in the tube recorded. Usually 3 tubes were run at one time.

The control tube containing only $C_8$ ABSA was held at 220° C for 6.5 hours until the pressure reached 20 psi and stopped increasing. Hydroquinone (0.05 g) plus $C_8$ ABSA (1 g) in a similar tube reached a maximum pressure of 22 psi in 6.5 hours. The infrared spectra of the two products were almost identical and showed that they were essentially spirodilactones and contained a trace of anhydride. A similar run containing dimethylaniline (0.03 g) and $C_8$ ABSA (1 g) reached a pressure of 24 psi in 2 hours. The infrared spectrum was that of the spirodilactone. All runs were carried out in the same oil bath maintained at 220° C. The presence of $CO_2$ in the vapor was shown by analysis with a Fischer gas partitioner.

A series of such tests was carried out with a variety of bases and at a variety of temperatures without catalyst. The results are shown in the following Table I.

TABLE I

| Test | Additive | Weight, % | Temp., °C | Time, hrs | Pressure, psi | Anhydride Present in SDL[1] by IR |
|---|---|---|---|---|---|---|
| 1 | Pyridine | 3 | 220 | 0.7 | 24 | None |
| 2 | 2,2'-Bipyridyl | 3 | 220 | 1 | 23 | None |
| 3 | Benzyl trimethyl- | | | | | |

TABLE I-continued

| Test | Additive | Weight, % | Temp., °C | Time, hrs | Pressure, psi | Anhydride Present in SDL[1] by IR |
|------|----------|-----------|-----------|-----------|---------------|-----------------------------------|
|      | ammonium hydroxide | 5 | 180 | 2 | 28 | None |
| 4    | N,N-dimethyldodecylamine | 10 | 200 | 1 | 23 | None |
| 5    | Octanoic acid | 5 | 200 | 6 | 21 | Trace |
| 6    | None | — | 200 | 21 | 23 | Moderate |
| 7    | None | — | 220 | 6 | 21 | Trace |
| 8    | None | — | 240 | 4 | 23 | None[2] |
| 9    | None | — | 255 | 2 | 31 | None[3] |

[1]Spirodilactone
[2]After 5 hours
[3]After 3.5 hours

The above results show that a variety of tertiary amines and quaternary ammonium salts will catalyze the conversion of the ABSA to the spirodilactones. On the other hand, organic acids and free radical inhibitors do not affect the reaction — the product being spirodilactone as in a control without any additive. Acids such as toluene sulfonic acid caused evolution of $CO_2$, but the spirodilactone formation was low. Zinc chloride gave a mixture of spirodilactone and decomposition products. Bases such as sodium hydroxide and potassium cyanide also catalyzed the decarboxylation of ABSA, but they caused the formation of some tarry by-products. Sodium hydride gave a product containing a spirodilactone and by-products as well.

EXAMPLE 5

Spirodilactone from $C_8$ Alkyl Bis(succinic Anhydride)

Octyl bis(succinic anhydride) was heated with 10 weight percent N,N-dimethyldodecylamine at 200° C in the Fischer-Porter tube and associated equipment described above. After about 1 hour the pressure remained constant, and heating was continued for another 2.5 hours. The infrared spectrum of the product was characteristic of the spirodilactone.

The following examples show the preparation of keto diesters and keto diacids and uses thereof.

EXAMPLE 6

Di(n-Octyl) Ester of the Spirodilactone from $C_8$ ABSA

The spirodilactone from $C_8$ ABSA (10 g, 0.038 mol) was added to toluene (20 ml) containing n-octanol (12.9 g, 0.099 mol) and p-toluene sulfonic acid (0.15 g). The mixture was contained in a 100-ml round-bottom flask equipped with a Dean-Stark trap, condenser and a side arm to remove samples. The system was heated under reflux for 3.5 hours, but the infrared spectra indicated that the reaction was complete after about 5 minutes of refluxing. The mixture was cooled and extracted with 10% aqueous caustic. The organic phase was dried over magnesium sulfate, filtered, and distilled to remove toluene and excess octanol. The residue weighed 15.7 g for an 82 mol percent yield. The product was distilled at a bath temperature of 160° C and a vacuum of $5 \times 10^{-3}$ mm Hg. The distilled keto diester was a clear, colorless liquid. It was characterized by its carbonyl absorption band in the infrared at 1730 cm$^{-1}$.

EXAMPLE 7

Di(n-Butyl) Ester of the Spirodilactone from $C_8$ ABSA

This diester was made by refluxing a solution containing the spirodilactone from $C_8$ ABSA (5.0 g, 0.019 mol), n-butanol (7.2 g, 0.097 mol), toluene (40 ml) and p-toluene-sulfonic acid (0.5 g). Water stopped evolving after about 1 hour under reflux. The cooled solution was extracted with 10% sodium bicarbonate, and the solvent was removed, leaving the di(n-butyl) ester of the keto diacid corresponding to the spirodilactone from $C_8$ ABSA. The keto diester product was characterized by mass spectrometry as having a molecular weight of 394 (theoretical molecular weight of 394), and infrared carbonyl absorption at 1730 cm$^{-1}$.

The di(n-octyl) ester prepared above was evaluated as a plasticizer. The results from various tests on polyvinyl chloride (PVC) plasticized by these materials are given below in Table II, along with values from PVC plasticized with 2 commercial plasticizers.

TABLE II

| Plasticizer | Color | Flex. Temp., °C | Tensile Properties | | | Shore Hardness 10 sec. | Soap Water Extr.[1] | Volatility[2] |
|-------------|-------|-----------------|--------------------|--|--|------------------------|---------------------|---------------|
|             |       |                 | 100% Modulus psi | Break Strength psi | Break Elongation % | | | |
| Prod. Ex. 6 | lt. yellow | −21 | 2000 | 2740 | 340 | 88 | 4.5 | 4.5 |
| DOP[3]      | lt. yellow | −23 | 1700 | 2730 | 350 | 84 | 6.7 | 26. |
| ODTM[4]     | colorless  | −21 | 2400 | 2720 | 300 | 91 | 1.9 | 3. |

[1]% loss in weight after 48 hours at 70° C
[2]% loss in weight after 90 hours at 105° C
[3]Dioctyl phthalate
[4]Tri (octyl/decyl) mellitate, prepared from commercial mixture of octanol & decanol

EXAMPLE 8

Keto Diacid from Spirodilactone from $C_8$ ABSA

The spirodilactone was heated in aqueous potassium hydroxide (pH 14) for about 1 hour. The cool solution was acidified to pH 1 with concentrated hydrochloric acid. The keto diacid formed as an oil. Its infrared spectrum had carbonyl absorption peaks at 1710 cm$^{-1}$ and 1740 cm$^{-1}$, corresponding to the keto diacid.

While the character of this invention has been described in detail with illustrative examples, this has been done by way of illustration only and without limitation of the invention. It will be apparent to those skilled in the art that modifications and variations of the illustrative examples may be made in the practice of the invention within the scope of the following claims.

I claim:

1. Polyvinyl chloride plastic compositions containing amounts sufficient to impart plasticizing properties of the cyclic keto esters of spirodilactones from alkenyl or alkyl bis(succinic anhydride) having the formula

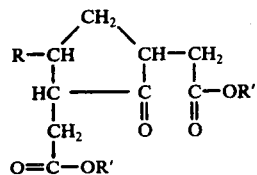

in which R is alkyl or alkenyl of 2 to 28 carbon atoms and R' groups, which may be the same or different, are hydrogen or alkyl groups of 1 to 8 carbon atoms each.

* * * * *